United States Patent [19]

Fujita

[11] 4,209,906
[45] Jul. 1, 1980

[54] ORTHODONTIC APPLIANCE (BRACKET AND LOCK PIN)

[76] Inventor: Kinya Fujita, 326 Nagasawa, Yokosuka-shi, Kanagawa-ken, Japan

[21] Appl. No.: 853,481

[22] Filed: Nov. 21, 1977

[30] Foreign Application Priority Data

Dec. 23, 1976 [JP] Japan ............................. 51-155429

[51] Int. Cl.² ............................................... A61C 7/00
[52] U.S. Cl. ...................................................... 433/11
[58] Field of Search .............................................. 32/14

[56] References Cited

U.S. PATENT DOCUMENTS

| | | | |
|---|---|---|---|
| 534,849 | 2/1895 | Angle | 32/14 A |
| 2,716,283 | 8/1955 | Atkinson | 32/14 A |
| 3,578,744 | 5/1971 | Wildman | 32/14 A |
| 3,975,824 | 8/1976 | Lee | 32/14 A |

Primary Examiner—Robert Peshock

Attorney, Agent, or Firm—Blanchard, Flynn, Thiel, Boutell & Tanis

[57] ABSTRACT

The present invention relates to the bracket of an orthodontic appliance for the treatment of dental malocclusion. Brackets of the present invention, which are used for securing the orthodontic wire, are all bonded to the internal sides of teeth, that is, the lingual or palatal side. The wire fixing slot of these brackets is formed either approximately parallel to the tooth axis so that the orthodontic wire may be inserted from the direction of the occlusal plane, or formed almost at a right angle to the tooth axis so that the wire may be inserted from the lingual or palatal side. The bracket has another groove for inserting a lock pin which can lock the fixed wire securely, so that the wire may be locked simply. The bracket is also provided with a shearing groove for cutting the lock pin when the wire is to be exchanged or removed, in order to facilitate the shearing operation with nippers, etc.

13 Claims, 24 Drawing Figures

ORTHODONTIC APPLIANCE (BRACKET AND LOCK PIN)

BACKGROUND OF THE INVENTION

The present invention relates to an orthodontic appliance for use in the treatment of dental malocclusion.

The newest and the most effective method of orthodontic treatment, the main purpose of which is to treat dental malocclusion, is the technique of firmly fixing a bracket to each tooth and inserting and fixing a U-shaped wire into these brackets in order to correct a malalignment of the teeth by the elastic force of this wire. For example, as shown in FIG. 2, when the upper jaw central incisor (1) protrudes abnormally toward outside as shown by the solid line, it is corrected to the state shown by the broken line, by a method in which a band (2) is applied to each tooth (1) as shown in FIG. 1 and brackets (3) are welded to the outsides of these bands (2), i.e. to their labial surfaces or buccal surfaces, then a curved orthodontic wire (4) is fixed to these brackets (3) to correct teeth malalignment by the elastic force of this wire (4). As examples of this method, there are the ribbon arch technique, the edgewise technique, the Begg technique, the universal technique, etc. Among them, the brackets of the edgewise technique are, as shown in FIG. 3, composed of a flange (5) like a metal net or a plate and the tip (6) is attached to this flange (5). A fixing groove (7) is formed in the tip (6), so that a rectangular wire (4) may be inserted horizontally. Wings (8) are formed on both sides of the groove, and a ligature wire (9) retains the wire 4 in the groove. In the Begg technique, brackets (3) are also composed of the flange (5) and the related tip (6), as shown in FIG. 4, but the fixing groove (7) is formed so that a wire (4) may be inserted vertically from the opposite side of the occlusal plane. In addition, a slot is made for insertion of a lock pin (10) shown by the broken line. This pin is inserted from the gingival side and the protruding lower edge of the inserted lock pin (10) is bent and fixed. The ribbon arch technique and the universal technique similar to the edgewise technique or the Begg technique.

The main disadvantage of these conventional methods is that the bracket (3) and wire (4) are visible clearly from the outside of the mouth when the mouth is opened, because the brackets (3) are bonded or welded to the outer surfaces of teeth (1) i.e. their labial or buccal sides. This detracts from the facial beauty of the patient and, accordingly, imposes a considerable psychological burden on the patients.

In conventional orthodontic treatment, there are some methods for treating malocclusion from the lingual or palatal side. Those are the lingual arch appliance or the palatal plate appliance. Those methods push several teeth simply from the inside by the auxiliary spring attached to the lingual arch or plate. Therefore, the cases which can be treated by those techniques are limited. Accordingly satisfactory results are not obtained in the treatment of all teeth. Neither is it possible to use the conventional bracket itself by bonding same to the inside surface of the teeth. For example, it is not only extremely difficult to bond the bracket for the edgewise technique or Begg technique to the inside surface of the teeth, but also insertion of a wire into the grooves of brackets from the gingival side, fixation by the ligature wire, and insertion and fixation of lock pins into brackets are extremely difficult or impossible. The same difficulties also exist in the ribbon arch technique or the universal technique.

BRIEF SUMMARY OF THE INVENTION

The primary purpose of the present invention is to reduce the mental burden of patients receiving orthodontic treatment and to improve the effect of the treatment by making the appliance invisible when the mouth is opened.

The second purpose of the invention is that the orthodontic treatment is carried out from the lingual or palatal side, to control all teeth movement in the oral cavity in three dimensions so that normal occlusion may be attained.

The third purpose of the present invention is to make exchanging of the wire easy when a wire with a larger elasticity is exchanged during the course of the treatment.

Additional purposes of the present invention and advantages thereof will be clarified by the following explanation on the attached Figures.

DETAILED DESCRIPTION

Figure 1:
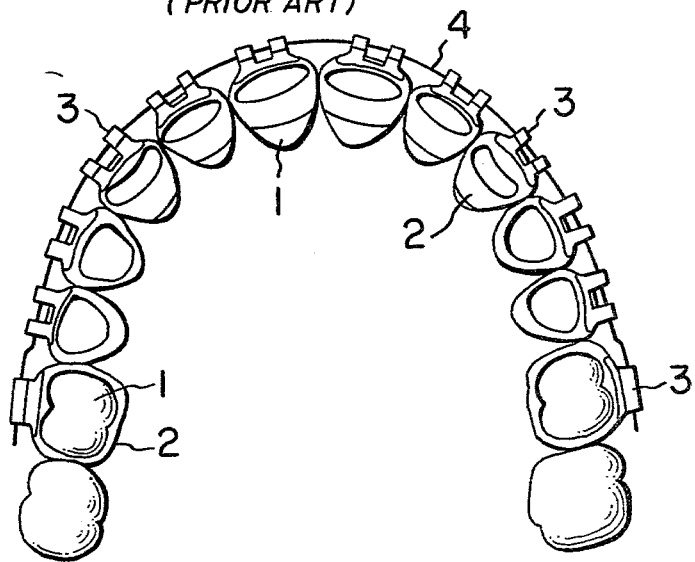
FIG. 1 is an illustration of a conventional orthodontic treatment technique.
Figure 2:
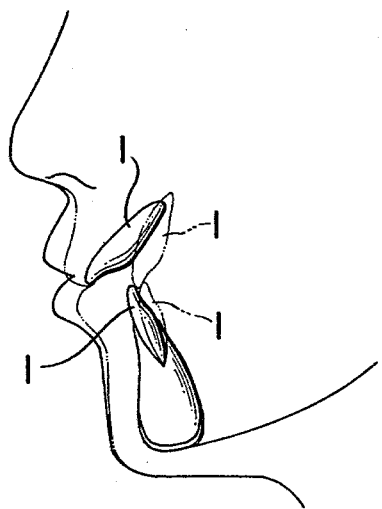
FIG. 2 illustrates the states of teeth before and after the orthodontic treatment.
Figure 3:
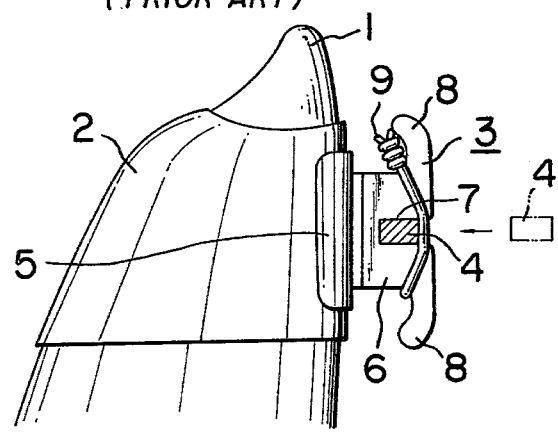
FIG. 3 is a side view illustrating the edgewise technique.
Figure 4:
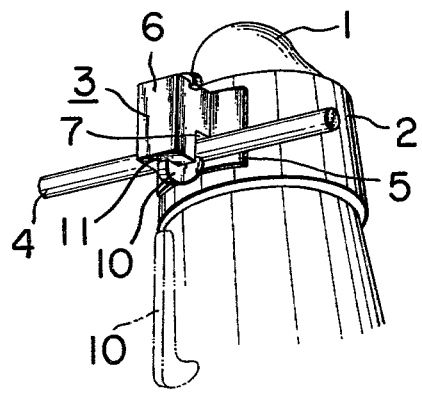
FIG. 4 is an oblique view of the Begg technique.
Figure 5:
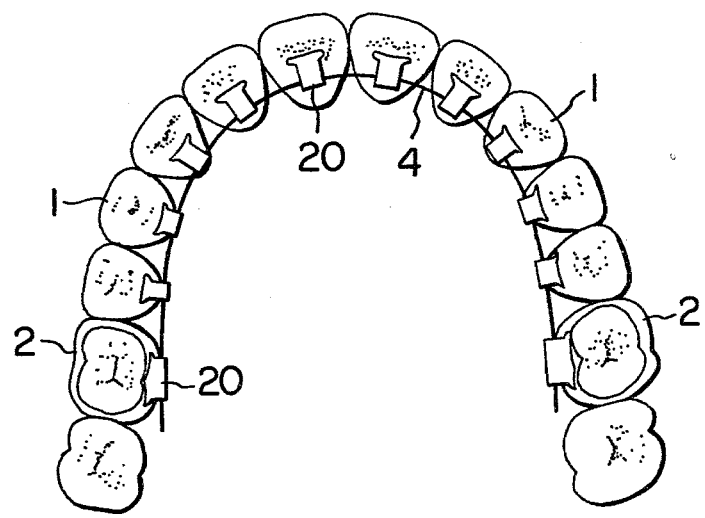
FIG. 5 is an illustration of an exemplary orthodontic treatment utilizing the appliance of the present invention.

FIG. 5 shows an orthodontic state using the appliance of the present invention. Brackets (20) are attached to the inside surfaces of the teeth (1), namely, the lingual or palatal sides. An orthodontic arch wire (4) is fixed to the brackets. On the molar teeth are secured the bands (2), to which the bracket is welded in most cases. On the other teeth (1), most of the brackets are bonded directly to the teeth (1).

Figure 6:
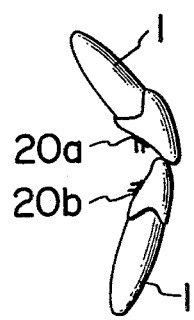
FIG. 6 illustrates two fundamental forms of the bracket of the present invention.

The brackets (20) are classified into two fundamental types according to the direction of the insertion of orthodontic arch wire (4). Namely, the bracket (20a) appearing in the upper side in FIG. 6 is a bracket of the first type into which a wire (4) is inserted vertically from the occlusal toward the gingival side. The bracket (20b) appearing in the lower side is a bracket the second type into which the wire (4) is inserted horizontally from the lingual or palatal side.

Figure 7:
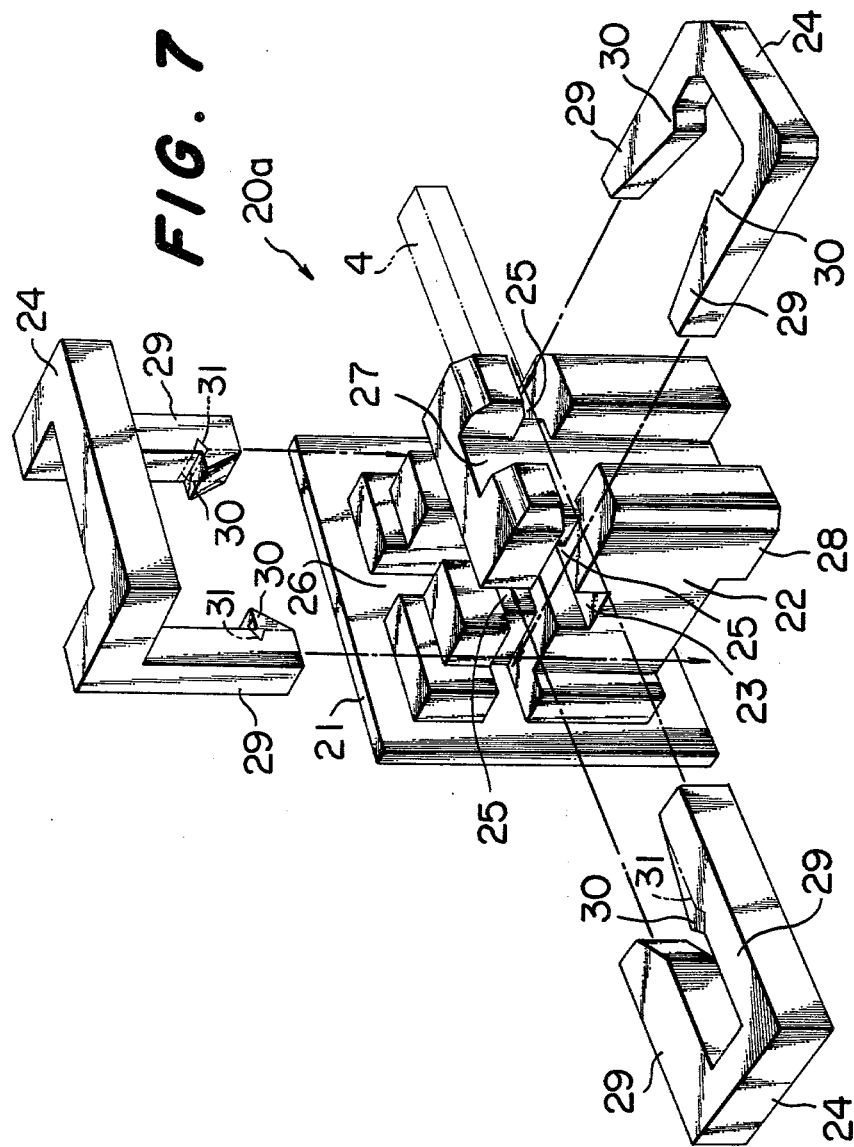
FIG. 7 is an oblique view of the first type bracket and lock pin of the present invention.

Referring to FIG. 7, the bracket (20a) of the first type of this invention is composed of a flange (21) and the related tip (22). When the flange (21) is directly bonded to tooth a (1), the flange is made of a mesh plate in order to improve the property of attachment. When it is spot welded to the band (2), thre flange (21) is made of a metal plate. The related tip (22) is made of plastic or metal material and is fixed to the above-mentioned flange (21) or is unitary with it. On the tip of the first type bracket (20a), a wire fixing slot (23) is formed so as to fix a wire (4) vertically from the occlusal side toward the gingival side. Namely, wire fixing slot (23) is formed in such a way that in the case of a mandible tooth, the wire (4) is inserted downwardly, while in case of upper jaw teeth, the wire (4) is inserted upwardly. The size of this fixing slot (23) is formed so as to be almost the same as the size of the rectangular wire (4). A groove (25) for a lock pin (24) is formed extending from the anterior to the lateral surface of the related tip (22). Also in the wire fixing slot (23), an inserting groove (25) is formed parallel to the wire. At the center of the edge of the base of the tip (22) is formed a vertical hole (26) for inserting and twisting a spring in order to adjust tooth axis (1) fixed to bracket (20a). At the center of the anterior surface of the tip (22), a vertical shearing groove (27) is formed for shearing the lock pin (24) with a nipper, etc. On the lower surface, a hook (28) is provided for hanging a rubber band, ligature wire, etc. The shape of the lock pin (24) used for the bracket (20a) shown in FIG. 7 is nearly U shape. The first type of lock pin (24) can be inserted into the inserting groove (25) at both lateral surfaces of the related tip (22). The inner sides of the legs (29) are tapered, and protruding stoppers (30) (30) are formed on the middle. The second type of lock pin (24) can be inserted parallel to the wire (4) and one of its leg (29) has the same width as that of the fixing groove (25) parallel to the wire (4) so that it may be inserted in it. The top edge of the shorter leg is tapered, while the other leg has a protruding (29) stopper (30) The third type of lock pin (24) can be inserted into wire fixing slot (23) from the occlusal direction and both its legs (29) (29) are offset at positions shifted at least the width of wire (4) so as not to collide with wire the (4). The insides of the legs have protruding stoppers (30) (30) whichever type of lock pin is used, it is pushed onto the tip 22 until it stops and removal thereof is elastically resisted when the lock pin is made of elastic material. But, when the lock pin is made of non-elastic material, the legs (29) (29) are widened for insertion. After insertion, they are closed to releasably lock same in place stop with pliers, etc.

Figure 8:
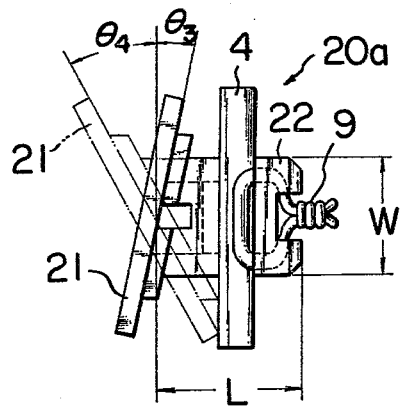
FIGS. 8 to 16 are plan views, side views and oblique views, respectively showing examples of variations of the first type bracket of the present invention.
Figure 9:
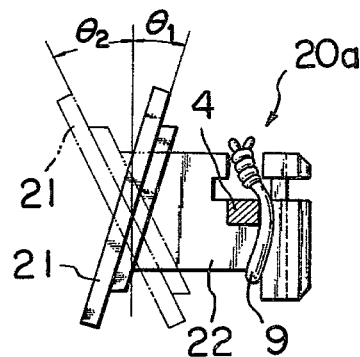
Figure 10:
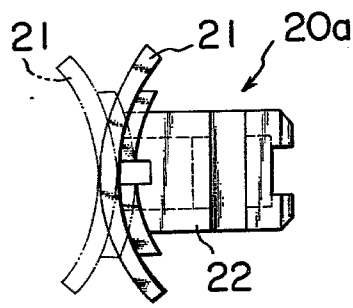
Figure 11:
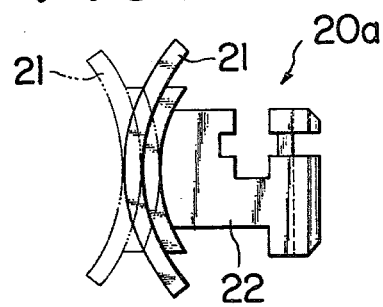
Figure 12:
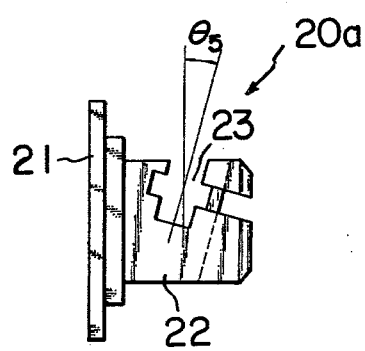
Figure 13:
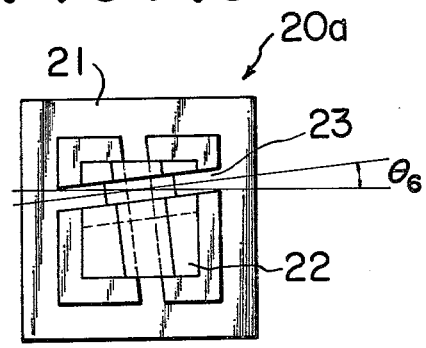

Brackets (20a) with different sizes should be used depending upon the size and shape of teeth such as incisors or molars and further depending upon the purpose of the use. For this purpose, several types of brackets (20a) with different widths (W) are prepared (FIG. 8). When the inside surface of each tooth (1) is plotted, the curve is not always smooth. Owing to this, the wire (4) has to be bent zigzig, but several kinds of brackets (20a) with different lengths (L) are provided (FIG. 8). The inside surface of each tooth (1) generally slopes and in some cases, the wire fixing slot (23) may need to be inclined according to the purpose of the treatment. For this purpose, as shown in FIG. 9, the flange (21) may be formed slantwise forward or backward to a vertical line by a certain angle ($\theta_1$) ($\theta_2$) or as shown in FIG. 8, slanted to the left or right at a certain angle ($\theta_3$) ($\theta_4$). Furthermore, as shown in FIGS. 10 and 11, it may be possible to make the flange (21) a curved surface to adjust same to the shape of the tooth (1). These angles can be made not only two dimensionally but also three dimensionally. FIG. 12 and FIG. 13 show respectively that the wire fixing slot (23) itself lies at an angle ($\theta_5$) to the vertical or lies at an angle ($\theta_6$) to the horizontal and this also may be formed in three dimensions.

Figure 14:
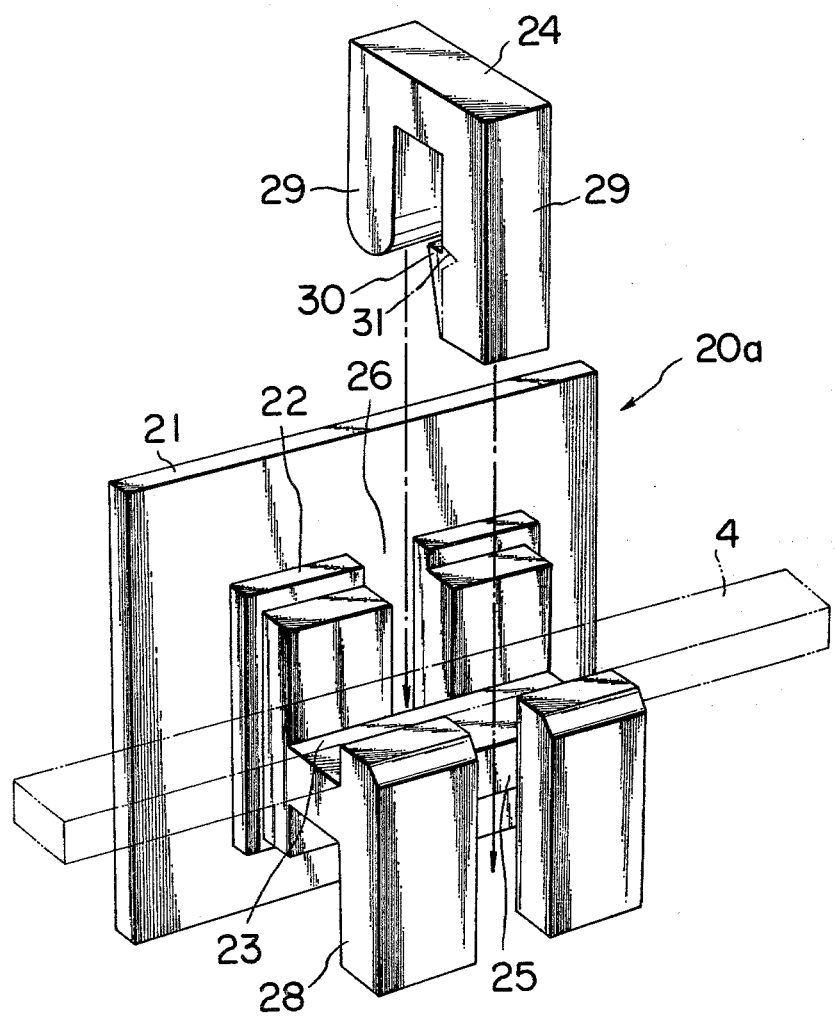
Figure 15:
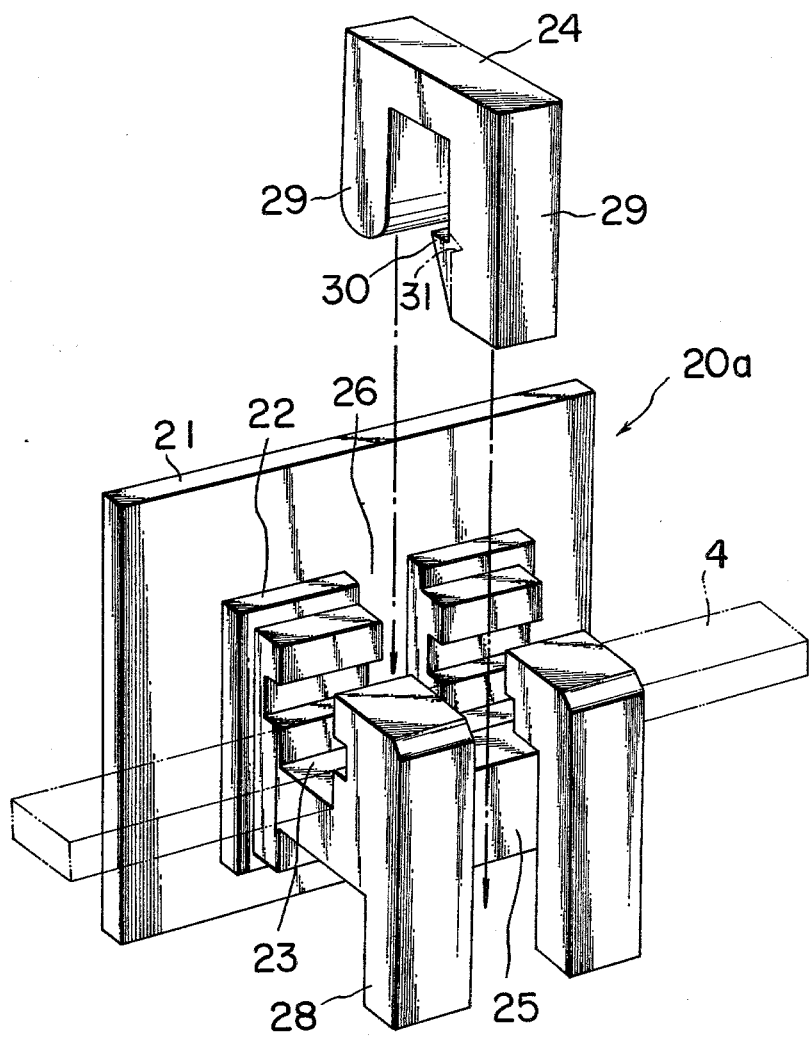
Figure 16:
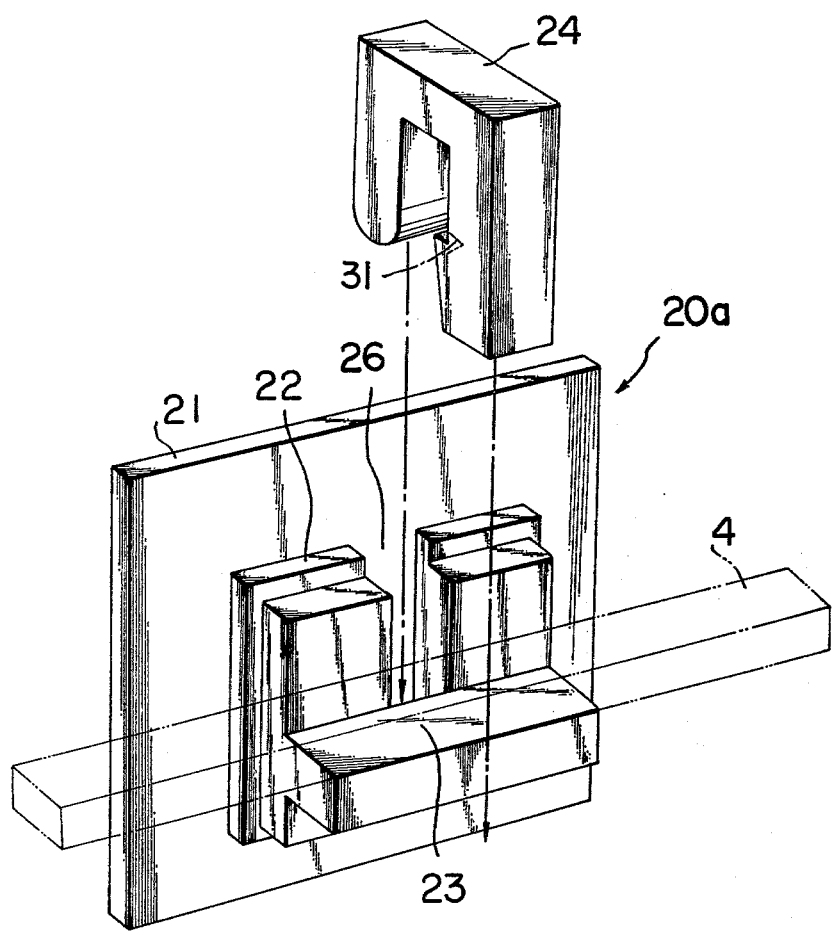

In FIGS. 14 and 15 are shown first type brackets (20a) but there is a difference in the way of locking the lock pin (24). Namely, the groove (25) for inserting lock pin (25) is formed vertically at the center of the anterior surface of the related tip (22) and a lock pin (24) is inserted and fixed from the occlusal plane toward the gingival side utilizing this groove (25) and the before mentioned angle regulating hole (26). The lock pin (24) used in this case is one having a protruding stopper (30) only on one leg (29). When a locked pin (24) is removed, the pin is cut along the fixing slot (23). It is also possible to build the tip (22) as shown in FIG. 16 wherein the hook (28) shown in FIGS. 14 and 15 is omitted.

Figure 17:
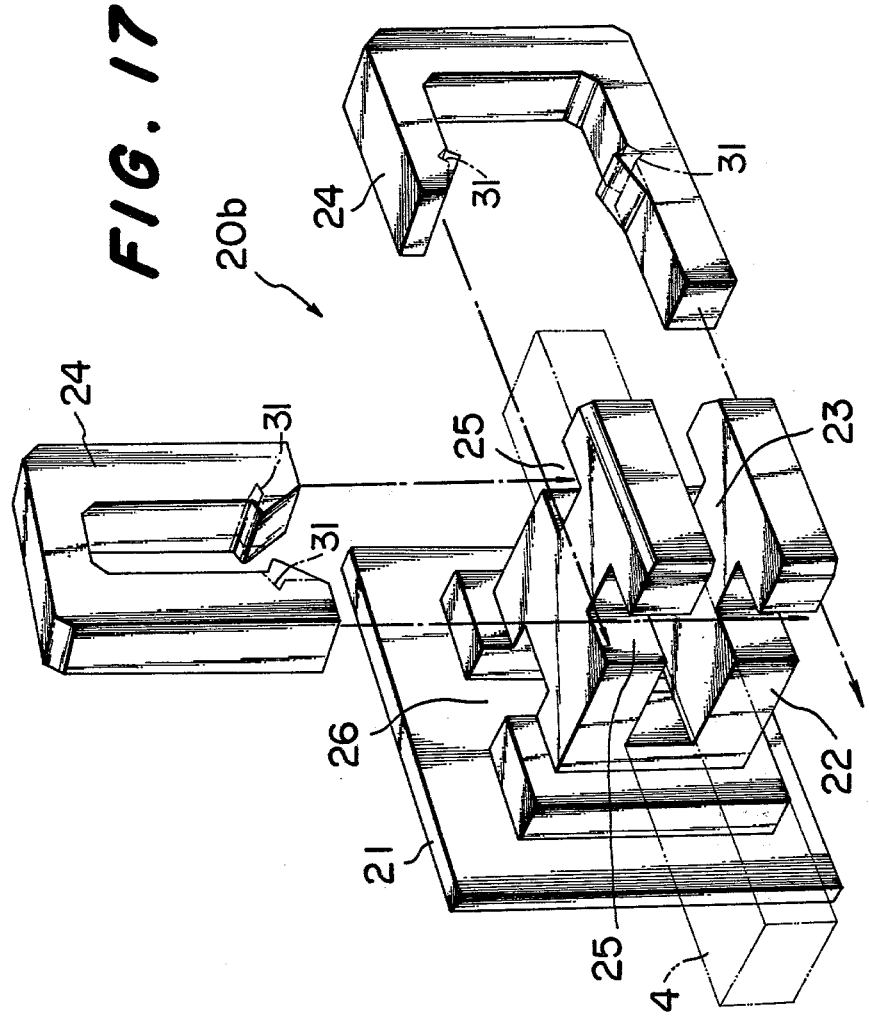
FIG. 17 is an oblique view of the second type bracket and lock pin of the present invention.
Figure 18:
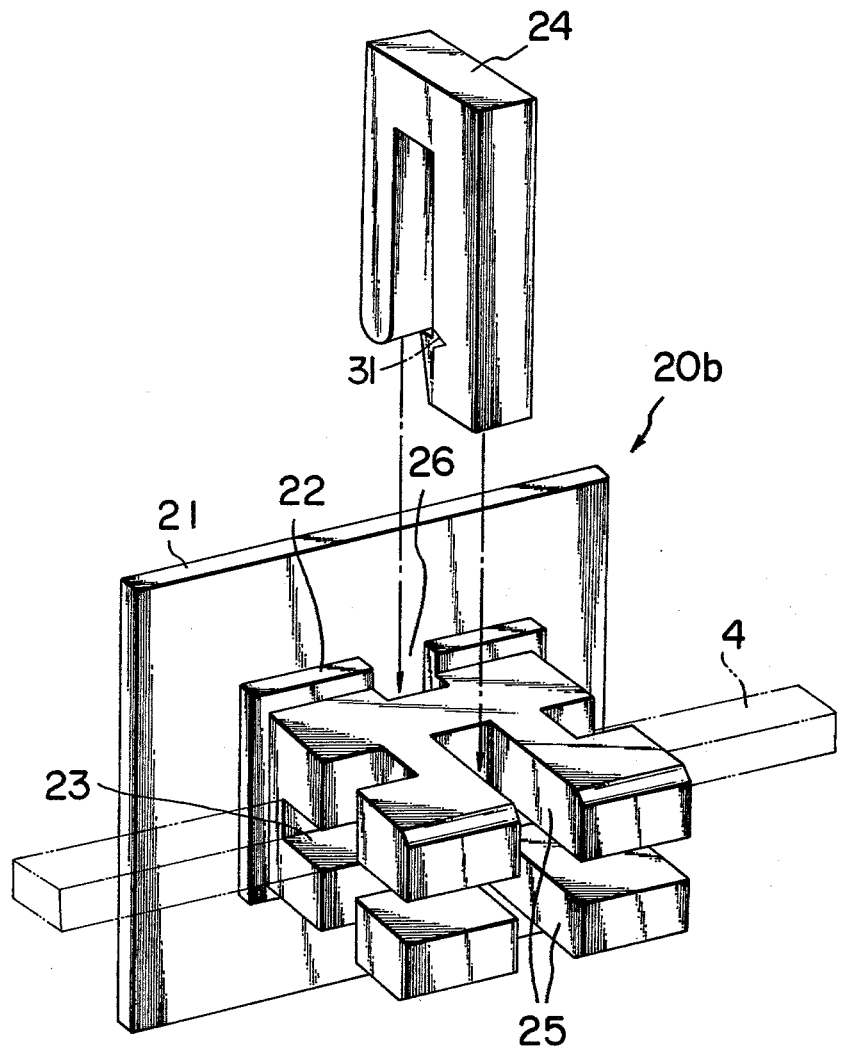
FIGS. 18 to 21 are the oblique views of examples of variations of the second type bracket respectively, according to the present invention.
Figure 19:
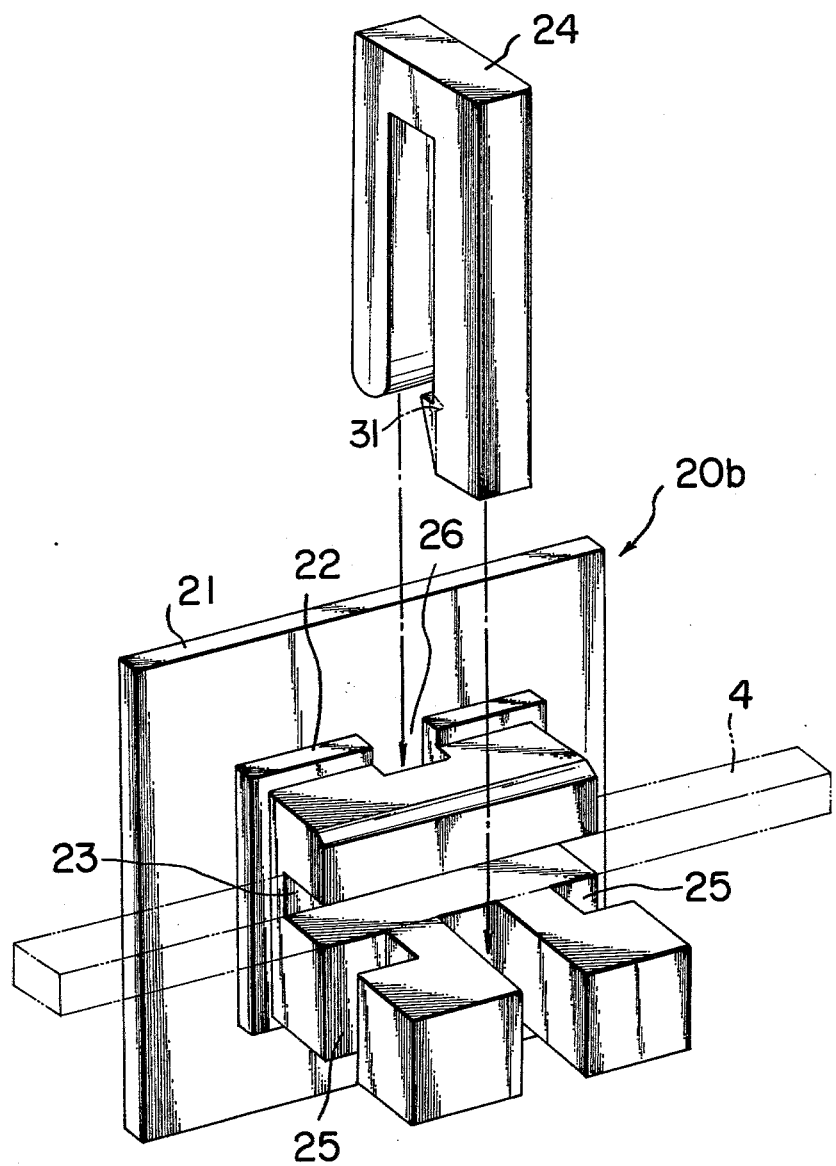
Figure 20:
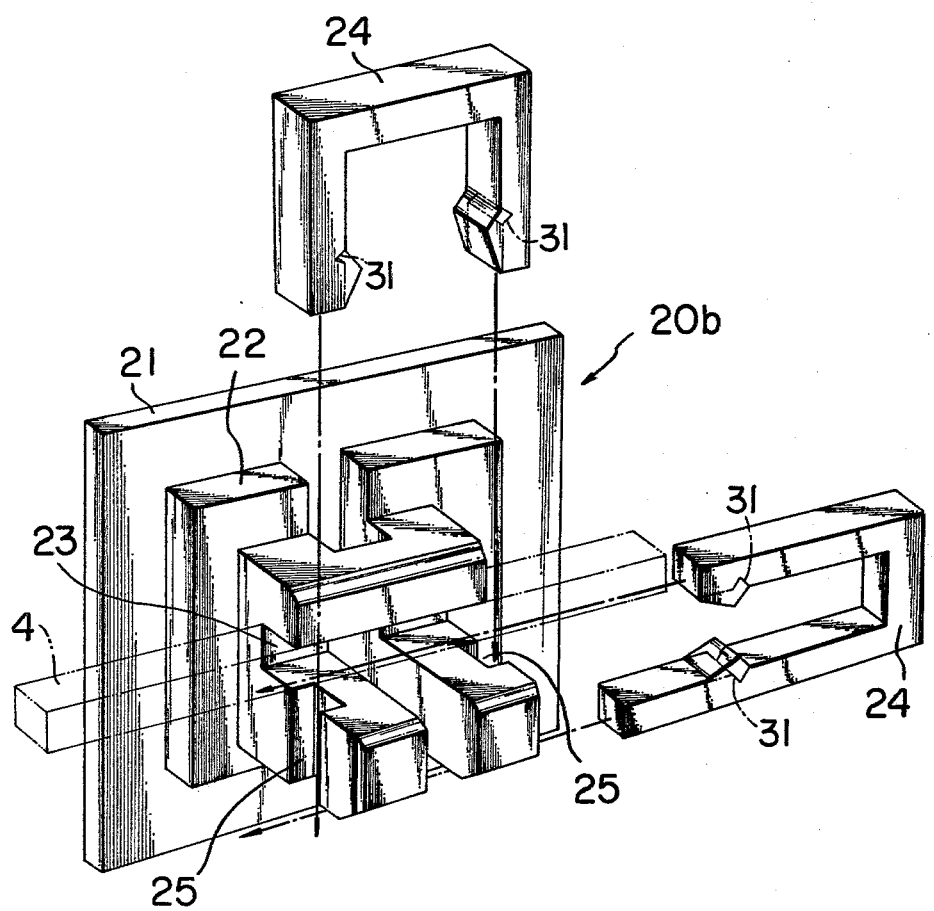
Figure 21:
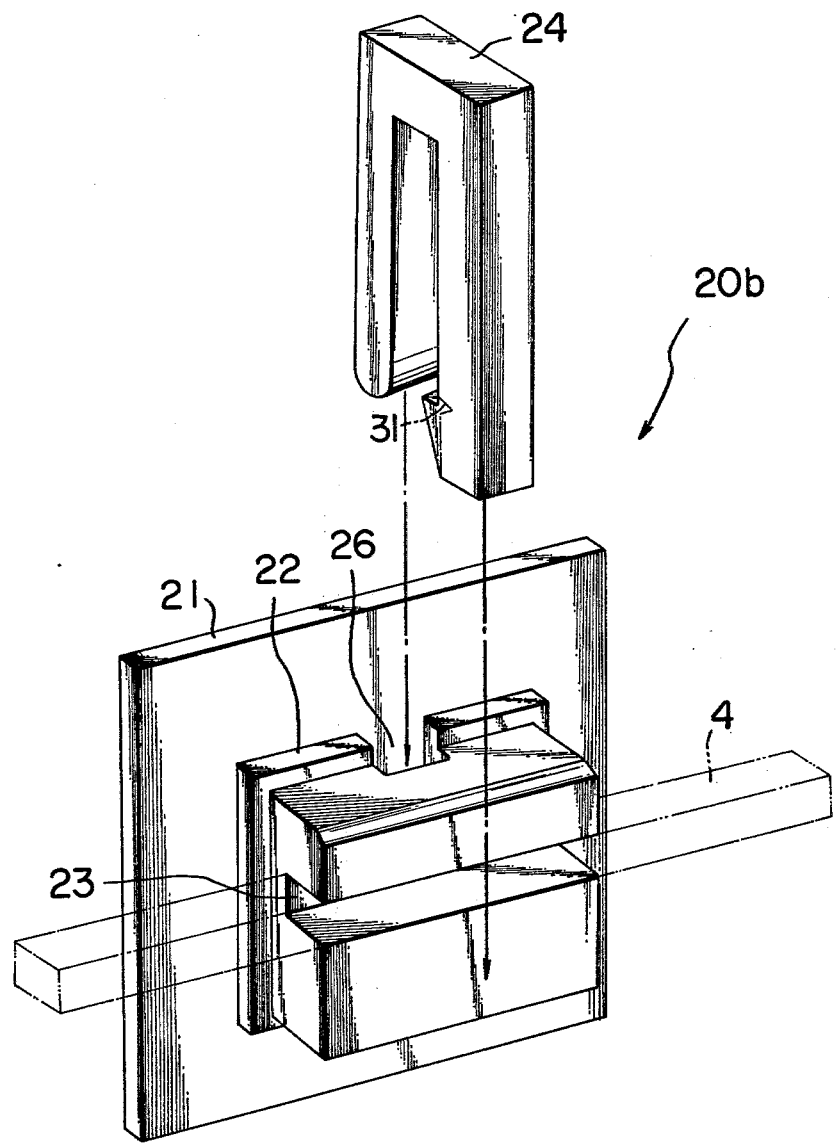

Next, FIG. 17 shows the second type bracket (20b). This type of bracket (20b) is also composed of the flange (21) and the related tip (22), but this bracket (20b) has the characteristic that the wire fixing slot (23) is formed so as to receive a wire (4) inserted laterally. Namely, the wire fixing slot (23) is formed in such a manner that a wire (4) is inserted from the lingual side of the mandibular teeth and from the palatal side of the maxillary teeth. The grooves (25) (25) for inserting the lock pin (24) are formed vertically at both sides of the related tip (22) and the lock pin is inserted into these grooves (25) (25) to lock from the occlusal plane, or the pin is inserted in the horizontal direction. This way of locking is principally quite same as in the case of the first type bracket (20a). FIG. 18 shows the case where a vertical pin groove (25) is further added in the anterior surface of the related tip (22) of the bracket (20b) in FIG. 17, and utilizing this groove (25), the angle regulating hole (26), and the lock pin (24) are inserted. FIG. 19 and FIG. 20 show the case where an upper part of the related tip (22) of the bracket (20b) in FIG. 18 is cut off. In this case, almost similar lock pin (24) to those in FIG. 17 and FIG. 18 is used for locking. FIG. 21 shows the case where each lower and upper part of the related tip (22) of the bracket (20b) in FIG. 18 is cut off.

In the second type bracket (20b), the examples given in FIGS. 8-13 are also applied directly as to width, and length of the related tip (22), angulation, and curved surface of flange (21), angulation of the wire fixing groove (23) and modification accompanying with the combination of these. The bracket (20) composed in this way is bonded directly to the inside surface of each tooth (1). Namely, a proper sort of bracket (20) is chosen according to the shape of the inside surface of tooth (1) as well as the purpose of the treatment, etc., and bonded from the lingual side to the tooth (1) of the lower jaw and from the palatal side to the tooth (1) of the upper jaw. Especially, in the case of molar teeth, sometimes band (2) is applied, to which the bracket (20) is welded. When brackets (20) are attached in this manner, a wire (4) to move the teeth (1) is curved and fixed into the wire fixing slot (23) of each bracket (20). Wire fixing slot (23) of the first type bracket (20a) has a merit that no deformation of the wire occurs when it is inserted and the operation is easy because the direction of insertion is from the occlusal plane toward the gingival side, i.e. in the direction of the tooth axis. Wire fixing slot (23) of the second type bracket (20b) has some difficulties in operation and the wire (4) may be deformed more or less because the direction of insertion is vertical to the tooth axis. However, this type has a merit of making it possible to make the shape of the related tip (22) much smaller. From these respects, the second type bracket (20b) is suitable for anterior teeth and the first type bracket (20a) is suitable for molar teeth, therefore they are used according to the kind of tooth (1) on which they are to be mounted.

Figure 22A:
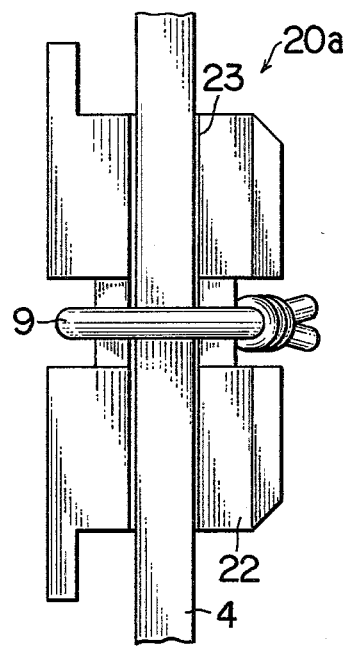
FIG. 22 is another variation of FIG. 1 type bracket, where (a) is the plan view, (b), the lateral view and (c), the front view.
Figure 22B:
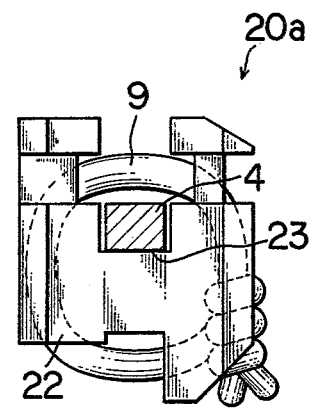
Figure 22C:
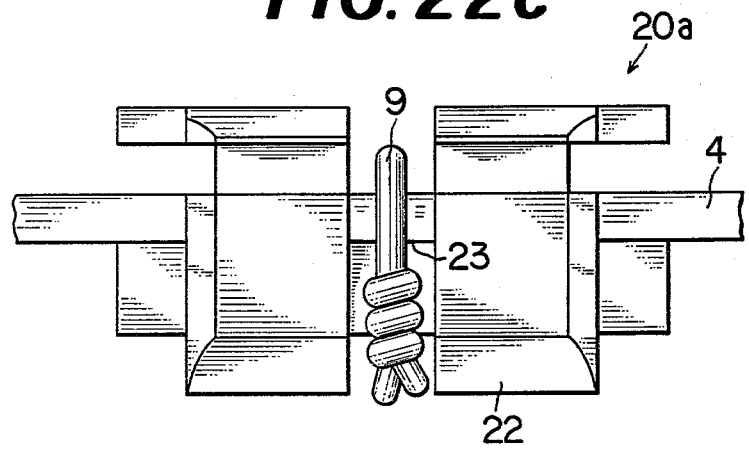

As described above, the bracket (20) is bonded to a tooth (1) and after inserting the wire (4), the lock pin (24) is inserted into the lock pin groove (25) to fix the wire (4). When the wire (4) is exchanged with one of higher elasticity or when the treatment is completed, the lock pin is cut at the site of the shearing groove (27) and the wire (4) is removed. Fixing the wire (4) is not limited only in case with the lock pin (24) but the conventional ligature wire (9) or a rubber band may be used as shown in FIG. 8, FIG. 9 and FIG. 22 or may be used along with the lock pin (24).

In this case, the wire fixing lock pin (24) is constructed of elastic material and the protruding stopper is provided at the inside surface of at least one of the legs. However, in other cases, the lock pin (24) is made of non-elastic material and at the same time, in place of the protruding stopper, the depressed hollow (31) is provided at the inside surface of at least one of the legs as shown by a broken line in FIGS. 7, 14, 15, 16, 17, 18, 19, 20 and 21. The lock pin (24) is bent at the site of the depressed hollow (31) to fix the wire (4) after the lock pin (24) has been inserted into the lock pin groove (25).

The embodiments of the invention in which an exclusive property or privilege is claimed are defined as follows:

1. An orthodontic bracket adapted for connection to an orthodontic arch wire, comprising: a flange having a surface shaped to conform to the shape of a portion of the lingual surface of the crown of a tooth; a tip portion projecting from the opposite surface of said flange and having an occlusal side at the top thereof, a gingival side at the bottom thereof, opposite lateral sides and a lingual side at the end thereof remote from said flange, said tip portion having a vertical groove located between said flange and said lingual side of said tip portion and opening to said occlusal side for receiving the orthodontic arch wire, said vertical groove extending between the opposite lateral sides of said tip portion and having a greater vertical depth than the thickness of the orthodontic arch wire and having a bottom wall on which the orthodontic arch wire can rest so that it extends generally parallel with the lingual surface of the tooth, said tip portion having horizontal groove means opening to said lingual side for receiving fastening means for retaining the orthodontic arch wire in the bottom of said vertical groove, said horizontal groove means intersecting said vertical groove at a location thereon vertically upwardly spaced from said bottom wall such that the orthodontic arch wire can be disposed entirely below said horizontal groove means.

2. An orthodontic bracket as claimed in claim 1, including a lock pin which is substantially U-shaped in plan view and has two spaced-apart substantially parallel substantially horizontal legs, said lock pin being receivable in said horizontal groove means so that said legs extend across said vertical groove above the position occupied by the orthodontic arch wire therein, said lock pin having a connecting web connecting said legs at the ends thereof remote from said flange, said horizontal groove means having an upright wall for engaging said connecting web to position said lock pin in said tip portion, said wall being located outwardly of the side of said vertical groove remote from said flange.

3. An orthodontic bracket as claimed in claim 2, in which the inner surface of at least one of said legs has a laterally inwardly projecting stopper engageable with the side of said wall opposite from said connecting web for locking said lock pin in place in said tip portion.

4. An orthodontic bracket as claimed in claim 2 in which the inner surface of at least one of said legs has a depressed hollow formed therein between the ends thereof and at a location adjacent the side of said wall opposite from said connecting web so that the portion of said leg beyond said depressed hollow can be bent laterally inwardly to lock said lock pin in place in said tip portion.

5. an orthodontic bracket as claimed in claim 1 in which said tip portion has a second vertical groove in the lingual side thereof and interesting said horizontal groove means so that said fastening means can be sheared by a tool.

6. An orthodontic bracket as claimed in claim 2 in which said tip portion has a second vertical groove in the lingual side thereof and intersecting said horizontal groove means so that said lock pin can be sheared by a tool.

7. An orthodontic bracket adapted for connection to an orthodontic arch wire, comprising: a flange shaped to conform to the shape of a portion of the lingual surface of the crown of a tooth; a tip portion projecting from the opposite surface of said flange and having an occlusal side at the top thereof, a gingival side at the bottom thereof, opposite lateral sides and a lingual side at the end thereof remote from said flange, said tip portion having a horizontal slot extending between the opposite lateral sides of said tip portion for receiving and holding the orthodontic arch wire so that the orthodontic arch wire extends horizontally generally parallel with the lingual surface of the tooth, said slot having a bottom support wall adapted to be positioned toward the gingiva and adapted to support said orthodontic arch wire, said slot having an open side, said tip portion having means defining an upright wire-inserting opening extending from said open side of said slot to said occlusal side of said tip portion so that the wire can be inserted through said wire-inserting opening into said slot, said tip portion also having horizontal lock pin groove means intersecting said slot and extending to said lingual side of said tip portion, said lock pin groove means comprising two substantially parallel, spaced-apart passageways and a transversely extending retaining wall associated with at least one of said passageways; a substantially U-shaped lock pin adapted to extend across said slot at a position above the position of the orthodontic arch wire for retaining the orthodontic arch wire in the bottom of said slot, said lock pin having two substantially parallel legs extending through said passageways and across the upper side of said slot in a direction substantially perpendicular to said flange with at least one of said legs having a portion engaging said retaining wall so that said lock pin is held in said lock pin groove means for retaining the orthodontic arch wire in said slot.

8. An orthodontic bracket adapted for connection to an orthodontic arch wire, comprising: a flange shaped to conform to the shape of a portion of the lingual surface of the crown of a tooth; a tip portion projecting from the opposite surface of said flange and having an occlusal side at the top thereof, a gingival side at the bottom thereof, opposite lateral sides and a lingual side at the end thereof remote from said flange, said tip portion having a horizontal slot extending between the opposite lateral sides of said tip portion for receiving and holding the orthodontic arch wire so that the orthodontic arch wire extends horizontally generally parallel with the lingual surface of the tooth, said slot having a bottom support wall adapted to be positioned toward the gingiva and adapted to support said orthodontic arch wire, said slot having an open side, said tip portion having means defining an upright wire-inserting opening extending from said open side of said slot to said occlusal side of said tip portion so that the wire can be inserted through said wire-inserting opening into said slot, said tip portion also having horizontal lock pin groove means intersecting said slot and extending to one lateral side of said tip portion, said lock pin groove means comprising two substantially parallel, spaced-apart passageways and a transversely extending retaining wall associated with at least one of said passageways; a substantially U-shaped lock pin adapted to extend across said slot at a position above the position of the orthodontic arch wire for retaining the orthodontic arch wire in the bottom of said slot, said lock pin having two substantially parallel legs extending through said passageways and in a direction substantially parallel to said flange with one of said legs overlying the upper side of said slot and with at least one of said legs having a portion engaging said retaining wall so that said lock pin is held in said lock pin groove means for retaining the orthodontic arch wire in said slot.

9. An orthodontic bracket adapted for connection to an orthodontic arch wire, comprising: a flange shaped to conform to the shape of a portion of the lingual surface of the crown of a tooth; a tip portion projecting from the opposite surface of said flange and having an occlusal side at the top thereof, a gingival side at the bottom thereof, opposite lateral sides and a lingual side at the end thereof remote from said flange, said tip portion having a horizontal slot extending between the opposite lateral sides of said tip portion for receiving and holding the orthodontic arch wire so that the orthodontic arch wire extends horizontally generally parallel with the lingual surface of the tooth, said slot having a bottom support wall adapted to be positioned toward the gingiva and adapted to support said orthodontic arch wire, said slot having an open side, said tip portion having means defining an upright wire-inserting opening extending from said open side of said slot to said occlusal side of said tip portion so that the wire can be inserted through said wire-inserting opening into said slot, said tip portion also having vertical lock pin groove means intersecting said slot and lying in a plane substantially parallel to said flange and extending to said occlusal side of said tip portion, said lock pin groove means comprising two substantially parallel, spaced-apart passageways and a transversely extending retaining wall associated with at least one of said passageways; a substantially U-shaped lock pin adapted to extend across said slot at a position above the position of the orthodontic arch wire for retaining the orthodontic arch wire in the bottom of said slot, said lock pin having two substantially parallel legs extending through said passageways with at least one of said legs having a portion engaging said retaining wall so that said lock pin is held in said lock pin groove means for retaining the orthodontic arch wire in said slot, said lock pin having a central connecting web connecting the upper ends of said legs and horizontally offset from said legs in a direction toward said lingual side of said tip portion, said central connecting web being slidable vertically in said wire-inserting opening.

10. An orthodontic bracket adapted for connection to an orthodontic arch wire, comprising: a flange shaped to conform to the shape of a portion of the lingual surface of the crown of a tooth; a tip portion projecting from the opposite surface of said flange and having an occlusal side at the top thereof, a gingival side at the bottom thereof, opposite lateral sides and a lingual side at the end thereof remote from said flange, said tip portion having a horizontal slot extending between the opposite lateral sides of said tip portion for receiving and holding the orthodontic arch wire so that the orthodontic arch wire extends horizontally generally parallel with the lingual surface of the tooth, said slot having a bottom support wall adapted to be positioned toward the gingiva and adapted to support said orthodontic arch wire, said slot having an open side, said tip portion having means defining a wire-inserting opening extending horizontally from said open side of said slot to said lingual side of said tip portion so that the wire can be inserted through said wire-inserting opening into said slot, said tip portion also having lock pin groove means intersecting said slot, said lock pin groove means comprising two substantially parallel, spaced-apart passageways and a transversely extending retaining wall associated with at least one of said passageways; a substantially U-shaped lock pin adapted to extend across said slot at a position above the position of the orthodontic arch wire for retaining the orthodontic arch wire in the bottom of said slot, said lock pin having two substantially parallel legs extending through said passageways with at least one of said legs having a portion engaging said retaining wall so that said lock pin is held in said lock pin groove means for retaining the orthodontic arch wire in said slot.

11. An orthodontic bracket as claimed in claim 10 in which said lock pin groove means in vertical and lies in a plane substantially parallel to said flange and extends to the occlusal side of said tip portion, the legs of said lock pin extending across the side of said slot remote from said flange.

12. An orthodontic bracket as claimed in claim 10 in which lock pin groove means is horizontal and lies in a plane substantially parallel to said flange and extends to one lateral side of said tip portion, said lock pin having a central connecting web connecting said legs and extending across the side of said slot remote from said flange.

13. An orthodontic bracket as claimed in claim 10 in which said lock pin groove means is vertical and extends to the occlusal side of said tip portion and lies in a plane substantially perpendicular to said flange, one of the legs of said lock pin extending across the side of said slot remote from said flange.

* * * * *